United States Patent [19]

Rickard

[11] 4,045,678
[45] Aug. 30, 1977

[54] MEDICAL RESTRAINT

[76] Inventor: Michael E. Rickard, 1324 Buena Vista, Pacific Grove, Calif. 93950

[21] Appl. No.: 751,772

[22] Filed: Dec. 16, 1976

Related U.S. Application Data

[63] Continuation-in-part of Ser. No. 553,396, Feb. 27, 1975, abandoned.

[51] Int. Cl.² ............................................. G03B 41/16
[52] U.S. Cl. .................................. 250/451; 250/468; 269/328
[58] Field of Search ...................... 250/451, 456, 468; 269/328

[56] References Cited

U.S. PATENT DOCUMENTS

| | | | |
|---|---|---|---|
| 1,453,473 | 5/1923 | McKenna | 250/451 |
| 3,293,430 | 12/1966 | Wustner | 250/451 |
| 3,302,021 | 1/1967 | Hardy | 250/451 |

Primary Examiner—Craig E. Church
Attorney, Agent, or Firm—Townsend and Townsend

[57] ABSTRACT

A restraint assembly for holding a portion of a patient in a fixed position on or relative to an X-ray table for the taking of X-rays is disclosed. The assembly comprises a restraint and restraint support. The restraint is usable with or without the restraint support and includes a platform which has a plurality of suction cups for mounting the platform to the X-ray table, the restraint support, or any other planar surface. A padded surface overlies at least a portion of the platform and is adapted to receive and support the portion of the patient to be restrained thereupon. A pair of sidewalls are attached to the platform on opposite sides of the padded surface and can be moved together to secure the portion of the patient to be restrained therebetween. If desired, a pair of slots can be formed in the platform on the opposite sides of the padded surface and a strap passed through the slots and around the portion of the patient to be restrained to further secure that portion of the patient and hold it in a fixed position. The restraint support includes a backplate that can be removably mounted perpendicular to the X-ray table and a frontplate slidably coupled parallel and adjacent to the backplate for vertical movement relative to the table. The restraint can be mounted to the frontplate of the support and then positioned a predetermined distance above the X-ray table.

16 Claims, 15 Drawing Figures

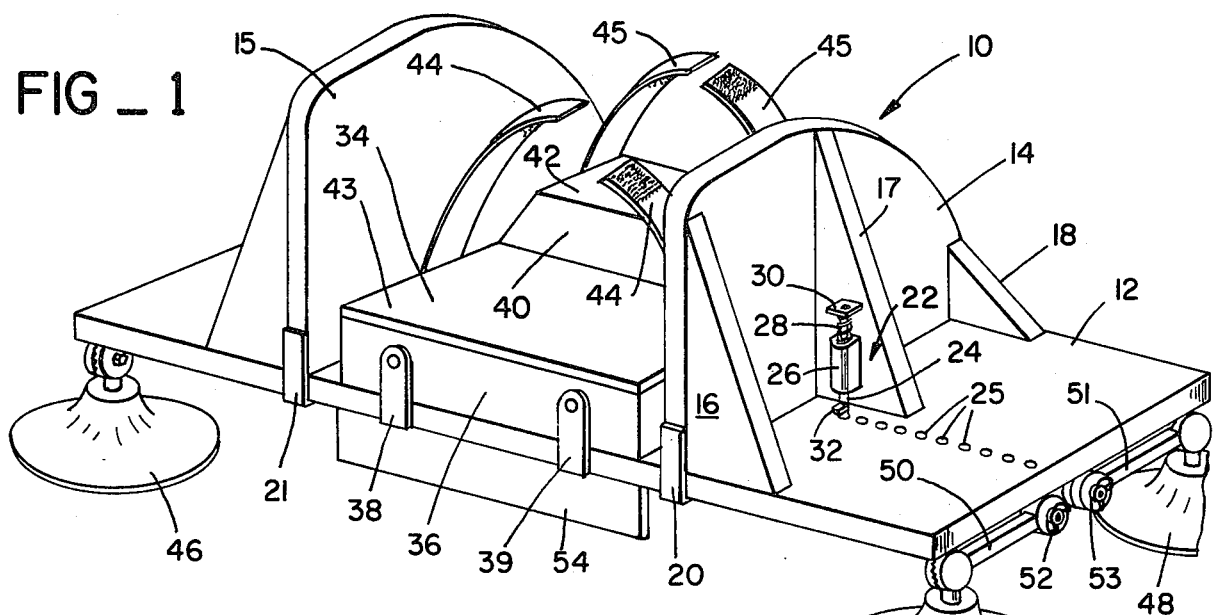
FIG_1
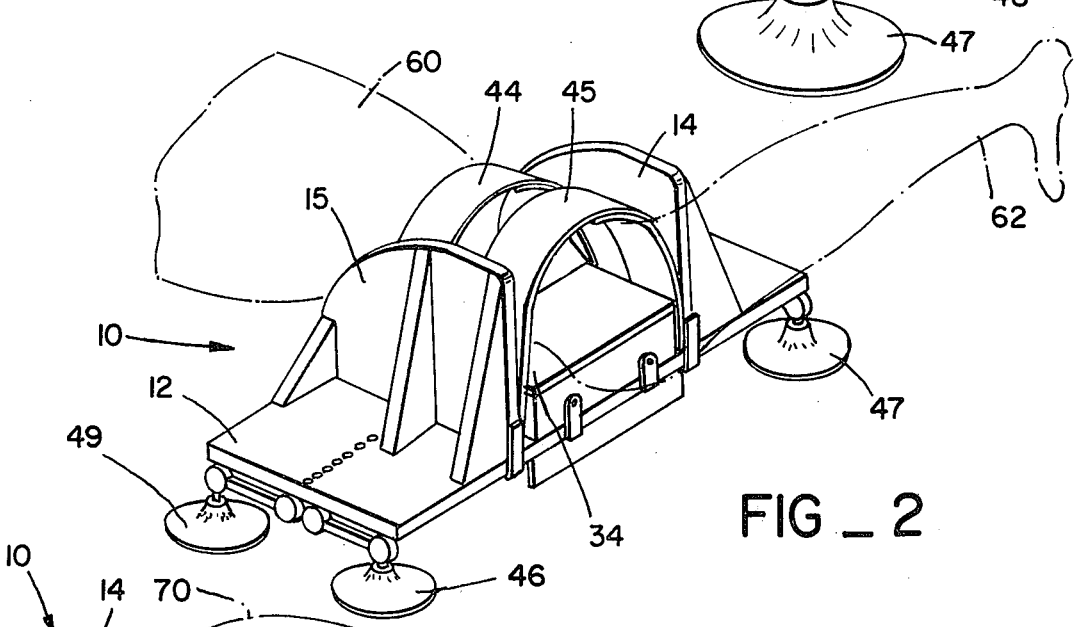
FIG_2
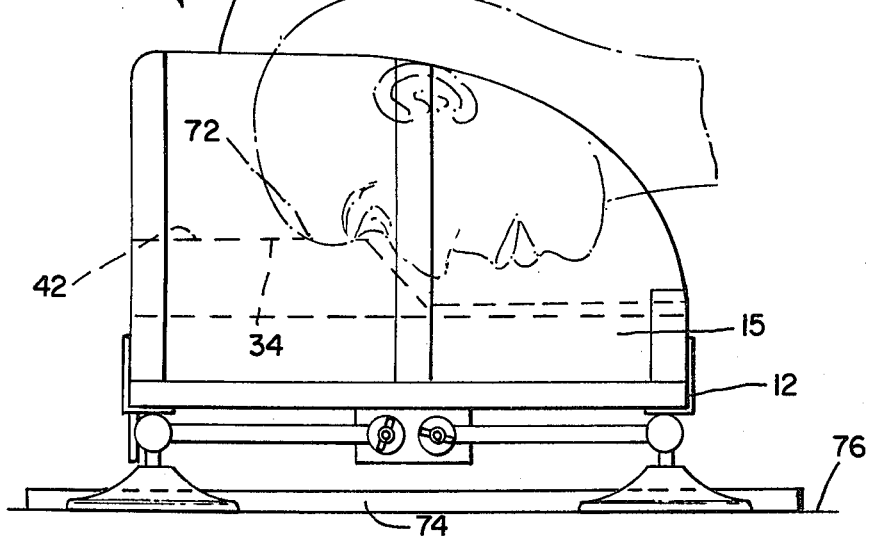
FIG_3

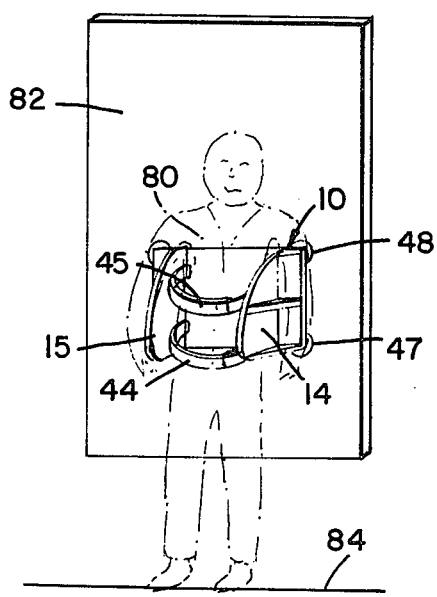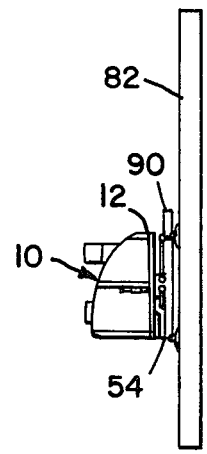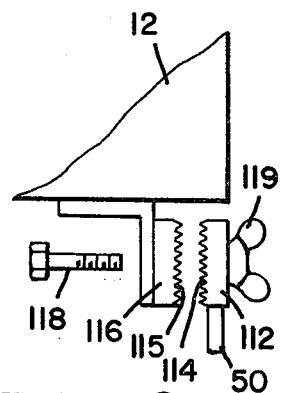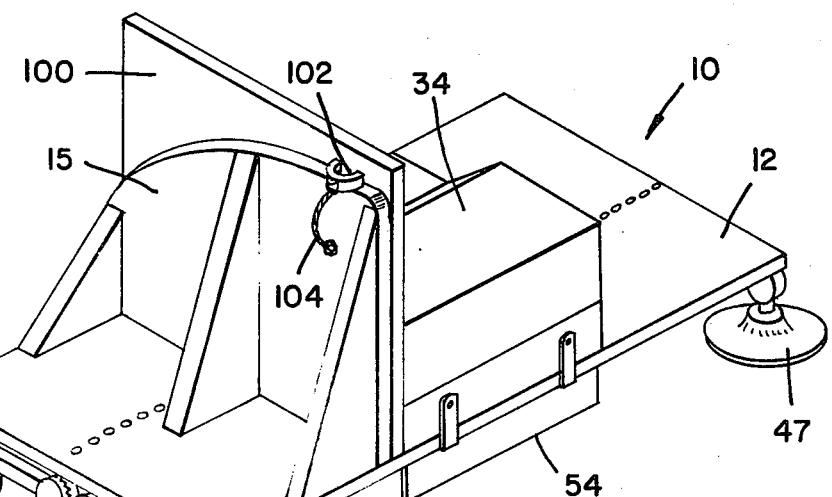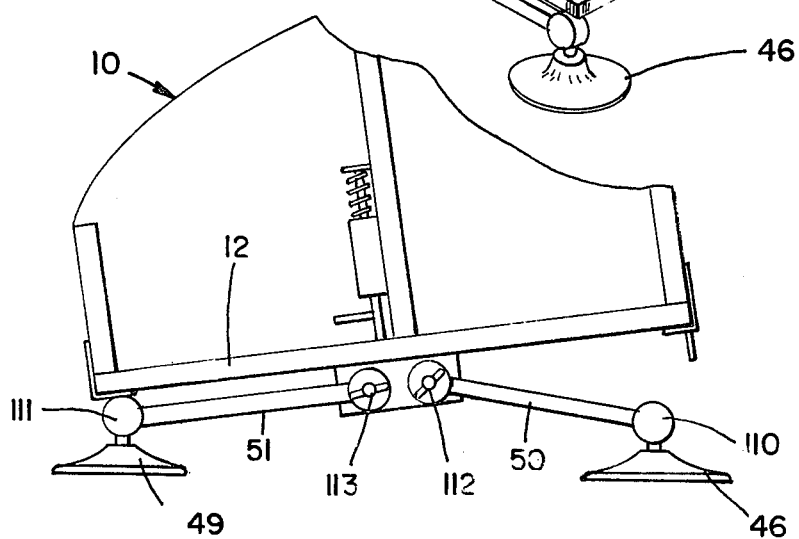

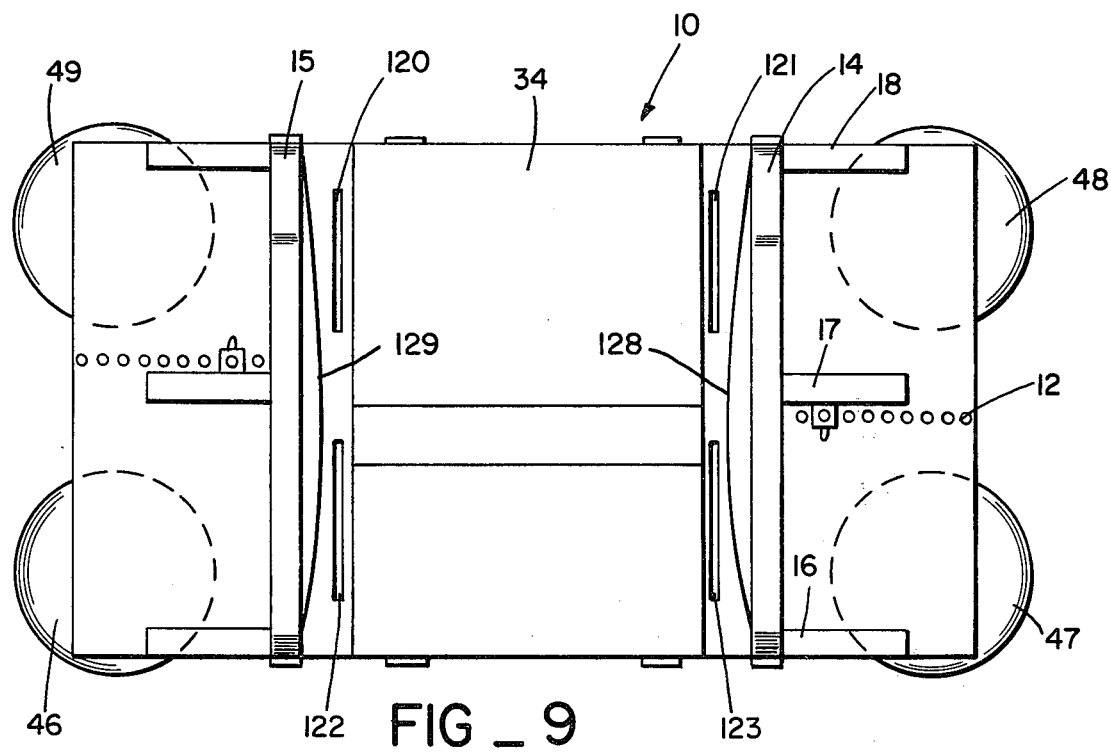
FIG_9
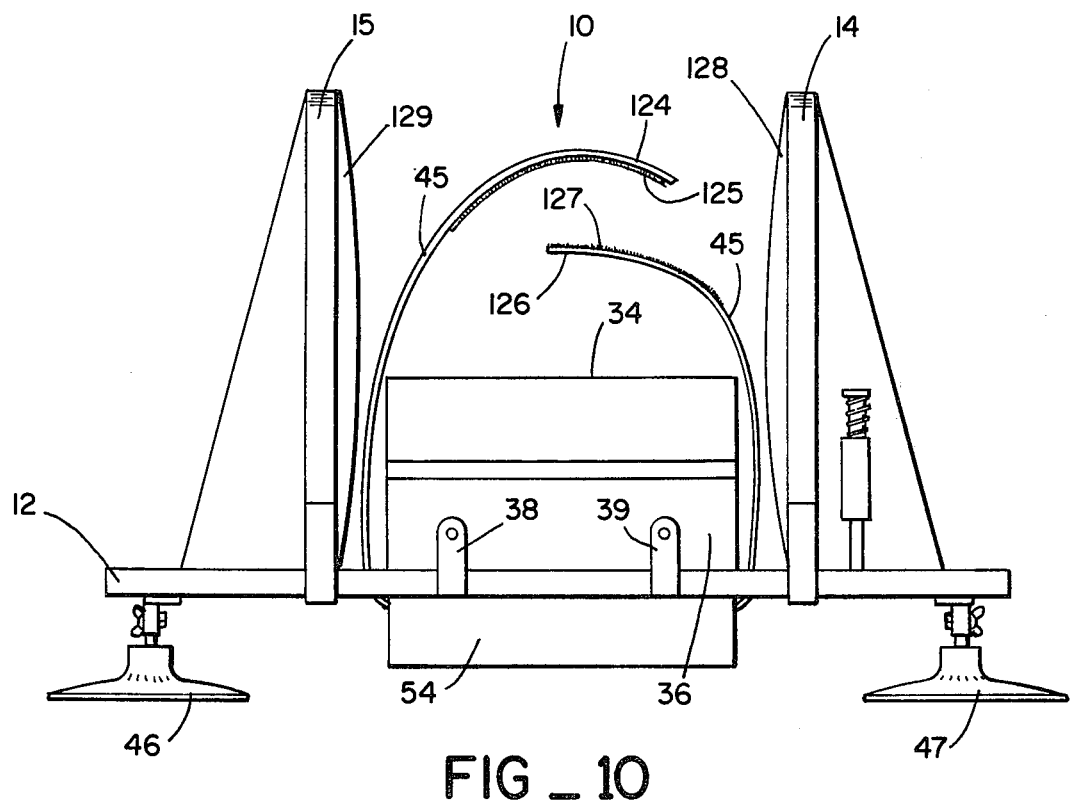
FIG_10

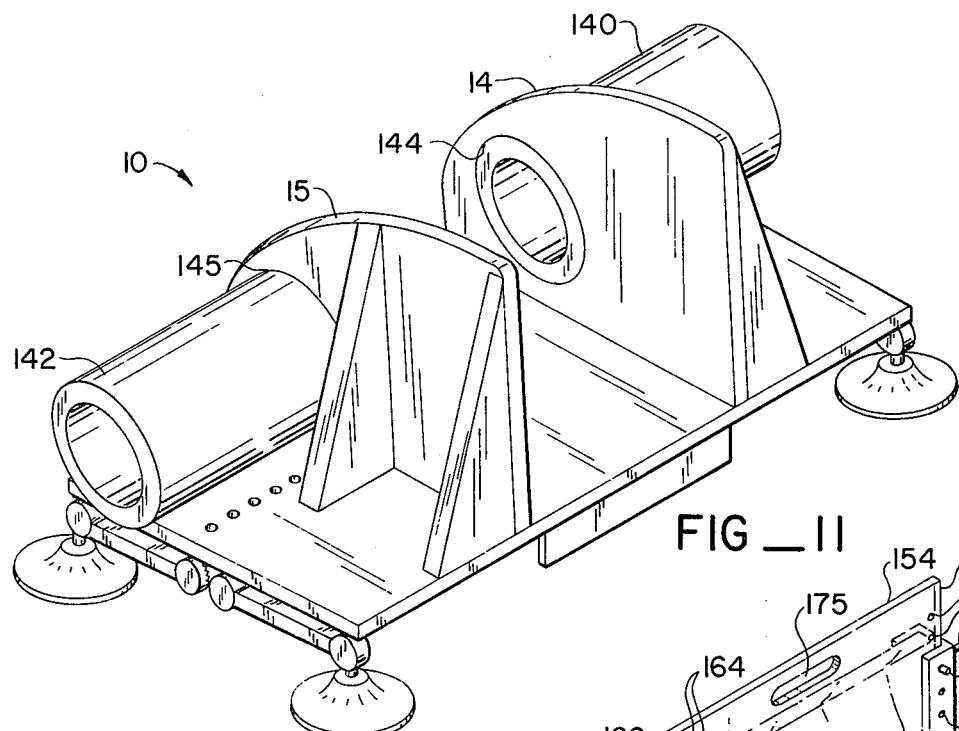
FIG_11
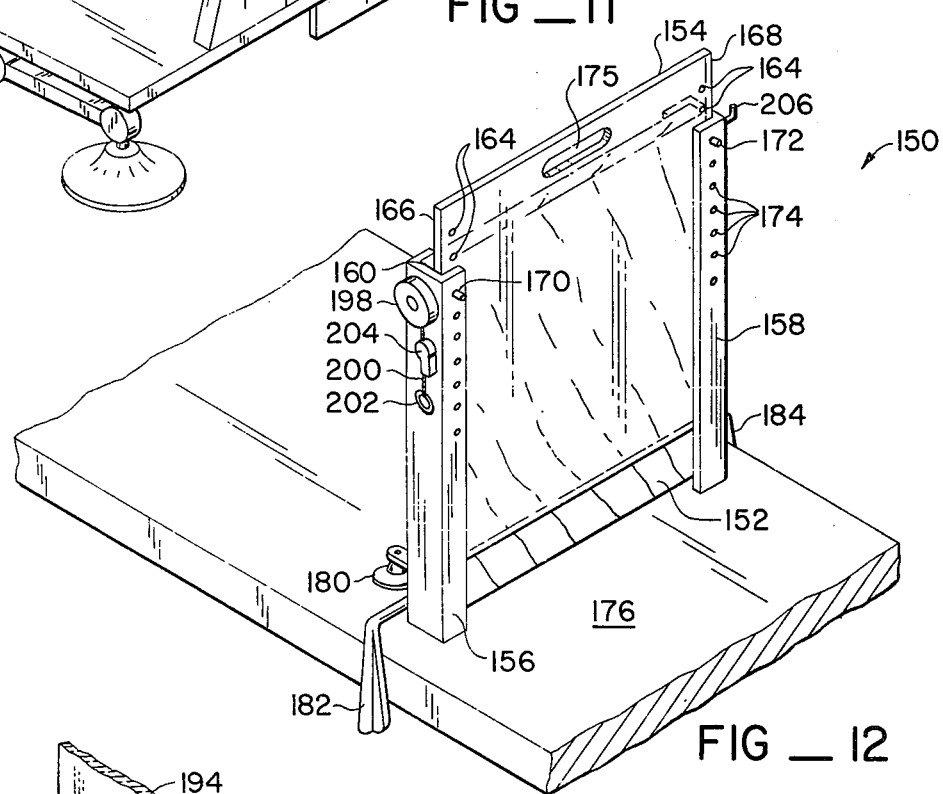
FIG_12
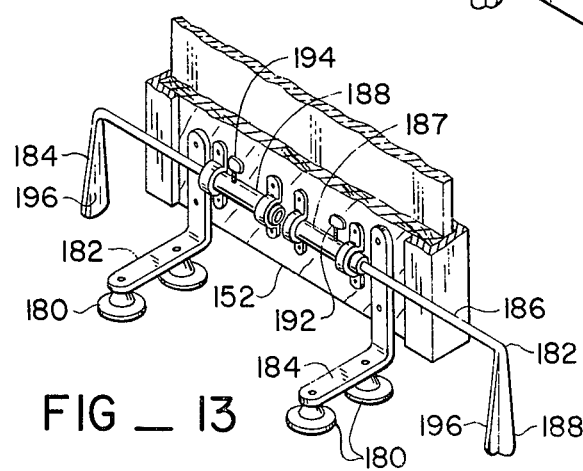
FIG_13

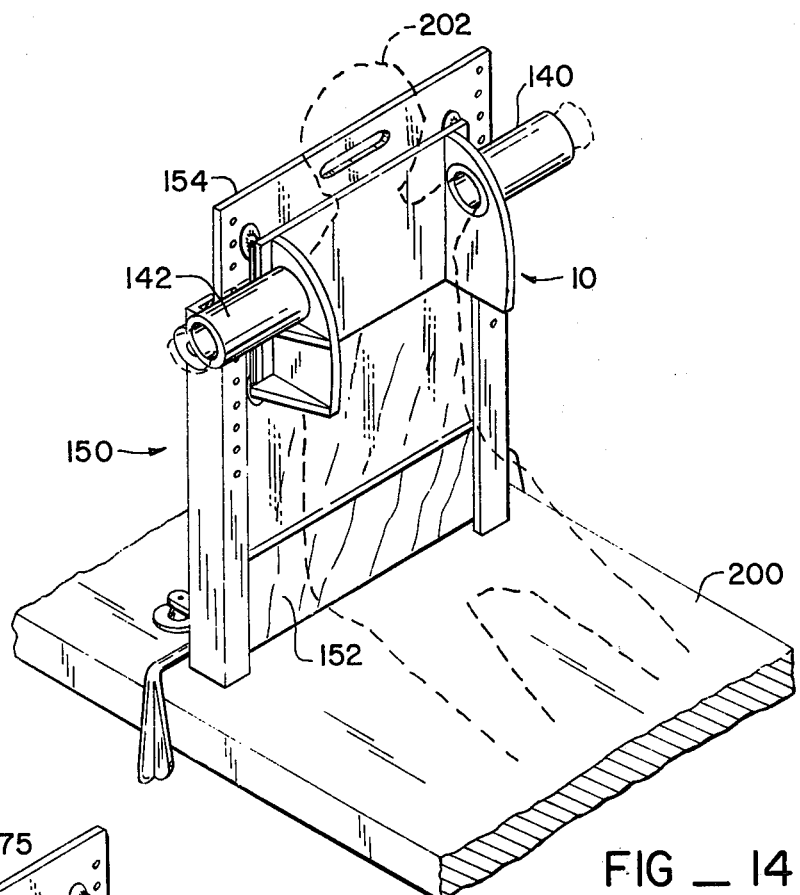
FIG _ 14
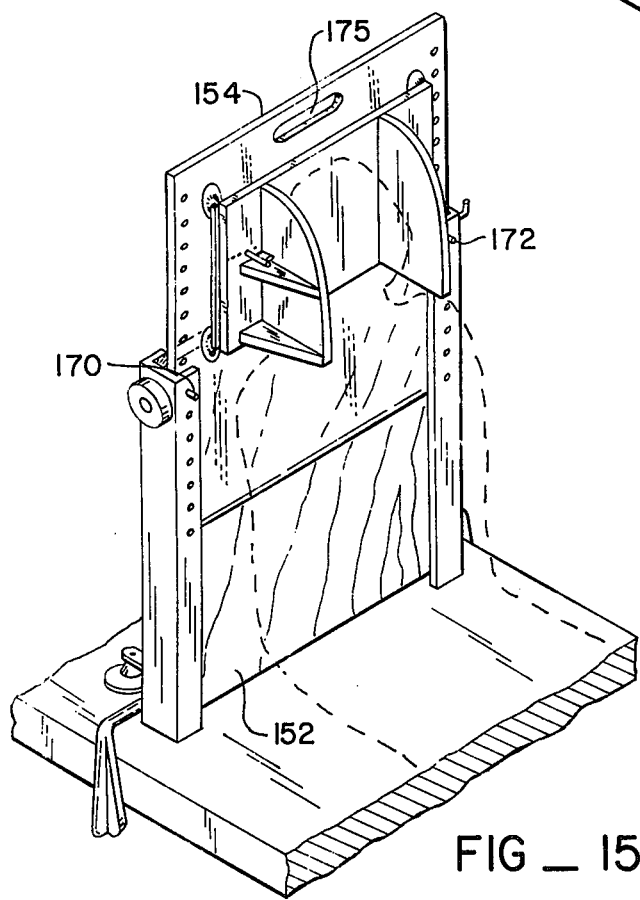
FIG _ 15

MEDICAL RESTRAINT

This is a continuation-in-part of prior copending application Ser. No. 553,396, filed Feb. 27, 1975 now abandoned.

BACKGROUND OF THE INVENTION

The present invention relates to a restraint and a restraint assembly which holds a portion of a patient such as the head or a limb in a fixed position for the taking of X-rays.

One of the difficult problems in the taking of X-rays of many injuries which occur in the joint of a patient, such as the knee or elbow, is opening up the space between bones of the joint so that the injured area can be clearly X-rayed. To perform such X-rays, it is often necessary to restrain one portion of the limb and manipulate the other portion to open up the joint so that the X-rays can be taken of the injured area. For example, with certain knee injuries, the thigh of the patient should be restrained just above the knee, and the lower leg manipulated at the ankle to open up the knee joint. In the past, such X-rays were sometimes taken by draping the leg of the patient over a pillow or similar support, but this technique does not always allow the knee to be manipulated as desired and the angles at which X-rays can be taken using this technique are quite limited. As a result, such X-rays were ordinarily taken by having one X-ray technician hold the thigh of the patient with another X-ray technician manipulating the leg.

Another problem in the taking of X-rays is holding the patient still so that a clear X-ray can be taken. This is often a problem with small infants who do not understand the necessity of remaining still as an X-ray is being taken. As a result, such infants must often be manually restrained as the X-ray is being taken and the hand of the technician holding the infant may appear in the X-ray and obscure it. Also, when head X-rays are to be taken, the head must be held completely still so that the X-ray will be sufficiently accurate for diagnosis, and even with adults, it is often necessary to restrain the heads so that the X-ray will be sufficiently accurate.

In each of the situations enumerated above, X-ray technicians are ordinarily used to restrain the patient so that the X-rays can be taken. As a result, an X-ray technician engaging in such practices is often near the X-ray machine as it is operated and subjected to the X-rays. Over a period of time, the effect of such X-rays is cumulative and the danger to the X-ray technician mounts. The practices discussed above which necessitate the use of an X-ray technician in the area of the X-ray machine as the X-rays are being taken is a severe hazard to such technicians, but one which is not easily avoided.

SUMMARY OF THE INVENTION

The present invention provides a restraint assembly for holding a portion of a patient in a fixed position on or relative to an X-ray table for the taking of X-rays. The assembly comprises a restraint and restraint support. The restraint is usable with or without the restraint support and includes a platform which has a plurality of suction cups for mounting the platform to the X-ray table, the restraint support, or any other planar surface. A padded surface overlies at least a portion of the platform and is adapted to receive and support the portion of the patient to be restrained thereupon. A pair of sidewalls are attached to the platform on opposite sides of the padded surface and can be moved together to secure the portion of the patient to be restrained therebetween. If desired, a pair of slots can be formed in the platform on the opposite sides of the padded surface and a strap passed through the slots and around the portion of the patient to be restrained to further secure that portion of the patient and hold it in a fixed position.

The restraint support includes a backplate that can be removably mounted perpendicular to the X-ray table and a frontplate slidably coupled parallel to and adjacent the backplate for vertical movement relative to the table. The restraint can be mounted to the frontplate of the support and then positioned a predetermined height above the X-ray table.

The restraint of the present invention can easily be attached to an X-ray table, the frontplate of the restraint support, or any other planar surface using the sunction cups provided for that purpose. X-ray cassettes can be placed on the X-ray table beneath the platform of the restraint or, if used with restraint support, the cassettes are placed between the platform and frontplate and held by a flange attached to the restraint. When the restraint is in place, a limb which is to be X-rayed can be attached to the restraint immediately above the injured joint to prevent movement of that portion of the limb. This allows the free portion of the limb to be manipulated as desired to open up the joint. The injured limb can be secured by the restraint at any angle so that X-rays of the joint can be taken at any desired angle. As a result, a complete set of such X-rays can be taken using the restraint of the present invention so that injuries to joints such as a knee can be accurately detected and diagnosed.

The restraint of the present invention can also be used for taking X-rays of the head. With the restraint of the present invention, the head of the patient can be rigidly fixed in position so that it cannot move and highly accurate X-rays can be taken. In addition, one sidewall of the restraint can be removed and an X-ray cassette secured to the other sidewall for taking head X-rays from the side.

The restraint of the present invention is particularly valuable in the taking of X-rays of children and adults whose reason is impaired and who cannot understand the necessity of remaining motionless as an X-ray is being taken. If a small child is to be X-rayed, his torso can be strapped in the restraint of the present invention so that he cannot move. The restraint will remain fixed to the X-ray table even if it is mounted in a vertical position. A flange can be provided on the underside of the restraint platform so that an X-ray cassette can be located between the platform and the X-ray table and held in position by the flange.

It is, at times, necessary that a child be positioned with his arms outstretched. In such a case, arm-receiving tubes are affixed to apertures located in the sidewalls of the restraint and concentric.

The restraint support is particularly useful in fixing and holding a patient or portion of the patient in an upright position. For example, the restraint support can be mounted to the X-ray table, the restraint attached to the frontplate of the support and, by vertically adjusting the frontplate, the restraint is positioned a desired height above the table. A child can then be strapped in the restraint of the present ivention, either in a sitting or standing, fixed, immobilized position for taking X-rays.

The restraint assembly is also advantageous in holding a patient's head in an upright, fixed position for obtaining upright X-rays of the skull and sinuses, for example, to determine fluid levels in the sinus.

The principal advantage of the present invention is that various types of X-rays can be taken without the necessity of an X-ray technician located near the X-ray machine. For X-rays of joints wherein the joint must be manipulated, only one X-ray technician is required to manipulate the joint and he can be located a significant distance from the position where the X-ray is actually taken. In other situations, no X-ray technician at all is required near where the X-ray is actually taken. Yet, the restraint of the present invention will result in far clearer and more accurate X-rays, and reduce the incidents in which the hand of an X-ray technician obscures the X-ray, without the danger of physical harm to the X-ray technician attendant with current X-ray techniques.

A further advantage of the present invention is that the portions of the patient to be restrained need not be confined to the horizontal surface of the X-ray table. Use of the restraint assembly allows a portion of the patient to be held in a fixed position vertically above the X-ray table. Moreover, the restraint need not be detached from the restraint support and reattached at a more convenient height relative to the X-ray table. The desired height of the restraint itself is quickly and easily obtained by merely adjusting the vertically slidable frontplate.

The novel features which are believed to be characteristic of the invention, both as to organization and method of operation, together with further objects and advantages thereof will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a perspective view of the medical restraint of the present invention;

FIG. 2 is a perspection view of the medical restraint of the present invention used for taking X-rays of a knee joint;

FIG. 3 is a side elevation view of the medical restraint of the present invention used to restrain the head of a patient for taking skull X-rays;

FIG. 4 is a perspective view of the medical restraint of the present invention used to restrain the torso of a child;

FIG. 5 is a side elevation view of the medical restraint attached to an X-ray table in the vertical position and supporting an X-ray cassette;

FIG. 6 is a perspective view of the medical restraint of the present invention adapted for use in taking X-rays from the side;

FIG. 7 is a side elevation view of the medical restraint in an angularly inclined configuration;

FIG. 8 is a fragmentary expanded view of the angular support structure of the medical restraint;

FIG. 9 is a top view of the medical restraint;

FIG. 10 is a front elevation view of the medical restraint;

FIG. 11 is a perspective view of the medical restraint of the present invention showing the addition of tubular sleeves for receiving and holding a patient's arms;

FIG. 12 is a perspective view of the restraint support of the present invention attached to an X-ray table;

FIG. 13 is a fragmentary perspective view of the restraint support of the present invention illustrating attachment to an X-ray table;

FIG. 14 is a perspective view of the restraint assembly of the present invention illustrating its use to restrain a child in a sitting position; and FIG. 15 is a perspective view of the restraint assembly of the present invention illustrating its use to restrain the head of a patient in an upright position for taking skull X-rays.

DESCRIPTION OF THE PREFERRED EMBODIMENT

The restraint assembly of the present invention is illustrated by way of FIGS. 14 and 15 and broadly includes restraint 10 and restraint support 150. The description of the present invention that follows will first discuss restraint 10 and its function with particular reference to FIGS. 1-11. Thereafter, the restraint support 150 will then be described with particular reference to FIGS. 12 and 13. Finally, the restraint and restraint support as a combined assembly will be described, referring particularly to FIGS. 14 and 15.

Turning now to FIGS. 1-10, the preferred embodiment of the medical restraint 10 of the present invention is illustrated, particularly by way of reference to FIG. 1. Restraint 10 includes a platform 12 having a pair of sidewalls 14, 15 disposed thereon. Each sidewall such as 14 has three braces 16, 17 and 18 which maintain the sidewall in a vertical position relative to platform 12. Angular brackets such as 20, 21 depend from sidewalls 14, 15 and have a flange portion (not visible) underlying platform 12 so that the sidewalls can move with respect to the platform.

Each sidewall 14 is provided with a locking mechanism such as 22 which fixes the position of the sidewall relative to platform 12. Locking mechanism 22 includes a depending bolt 24 which is adapted to project into and engage one of a plurality of slots 25 in platform 12. Bolt 24 is maintained in a vertical position by a sleeve 26 attached to angular support 17. Bolt 24 is biased downwardly by compression spring 28 which is in abutment with flange 30. Bolt 24 can be rasied upwardly against spring 28 using finger grip 32 to allow sidewall 14 to be positioned at any location along platform 12, or for removal of the sidewall from the platform altogether. In the preferred embodiment illustrated, both sidewalls 14 and 15 are movable, but in practice it may be desirable to have one such sidewall fixed and the other movable.

A foam pad 34 is mounted to a spacer 36 which is in turn mounted to platform 12 by detachable snap fasteners 38, 39. As illustrated, pad 34 is stepped at 40 to provide an upper step portion 42 and a lower step 43. A pair of straps 44, 45 project upwardly on both sides of pad 34 between the pad and the respective sidewalls 14, 15 and are adapted to be wrapped around the portion of the patient to be restrained, as illustrated in more detail hereinafter.

Platform 12 is adapted to be mounted to an X-ray table by meanns of a plurality of suction cups such as 46, 47 and 48. Suction cups 47, 48 are attached to armatures 50, 51 which are in turn connected to platform 12 by fasteners 52, 53, respectively, as will be illustrated in more detail hereinafter. Fasteners 52, 53 allow platform 12 to be fixed at an angle relative to the X-ray table. The level of platform 12 is raised sufficiently off the X-ray table so that an X-ray cassette (not shown) can be placed beneath the platform. If restraint 10 is to be used in a vertical configuration, and X-ray cassette can be held vertically between the platform and the X-ray table by flange 54.

The use of medical restraint 10 of the present invention in the taking of X-rays of a knee joint is illustrated by way of reference to FIG. 2. Platform 12 is fixed to the X-ray table (not shown) by the suction cups such as 46, 47, and 49. The thigh 60 of the patient is placed on the pad 34 of restraint 10, and the portion of the thigh immediately above the knee joint is fixed to the pad by straps 44, 45. To further fix thigh 60 in position, sidewalls 14, 15 can be moved inwardly to engage the thigh therebetween. Knee arthrograms (X-rays of the interior of the knee joint) can thus be taken by manipulating the leg of the patient at ankle 62. It is apparent that the position of the patient can be changed and the thigh fixed to medical restraint 10 at various angles to enable various types of arthrograms to be taken. When such arthrograms are taken, an X-ray technician need not be present to hold the thigh in position. The ankle can be manipulated by a technician standing a significant distance from the knee itself to minimize the dangers of X-ray exposure to the technician.

The use of medical restraint 10 in holding the head 70 of a patient perfectly still during the taking of an X-ray is illustrated by way of reference to FIG. 3. The head can be located so that the forehead 72 of the patient is on the upper step portion 42 of pad 34 so that the nose and mouth of the patient are exposed and the patient can breathe freely. Head 70 is restrained between sidewalls 14, 15 and the straps are not used. An X-ray cassette 74 is located on the X-ray table 76 beneath platform 12. In some X-ray tables, a recession is included in the table top into which the X-ray cassettes are inserted, and such X-ray tables can also be used with the restraint of the present invention. Cassette 74 can be removed and replaced without disturbing the patient so that several X-rays can easily be taken while the patient remains restrained.

The use of the medical restraint 10 of the present invention to restrain a child 80 against a vertical X-ray table 82 is illustrated by way of reference to FIG. 4. The child 80 stands on the floor 84, and restraint 10 is fixed to X-ray table 82 by the suction cups such as 47, 48 at chest height. Straps 44, 45 fix the child to restraint 10 and sidewalls 14, 15 are moved into position against the sides of the child. The arms of the child are free to drape over the outside of sidewalls 14, 15 and the child is held in position for the taking of chest X-rays.

As illustrated in FIG. 5, when medical restraint 10 of the present invention is fixed to an X-ray table 82 in its vertical configuration, an X-ray cassette 90 will fit between the platform 12 of the restraint and the surface of the X-ray table. The flange 54 depending from platform 12 holds X-ray cassette 90 in position so that the cassette can be removed and replaced and several X-rays can be taken without the necessity of removing the patient from the apparatus. Restraint 10 can be used in its vertical configuration to restrain children, as illustrated in FIG. 4, and also for the taking of head X-rays of adults in a vertical configuration.

It is often desirable to take X-rays from the side of a patient. If such X-rays were taken of a portion of a patient held by the medical restraint of the present invention with both sidewalls in place, the sidewalls would interfere with the X-ray exposure. To avoid this problem, at least one of the sidewalls of restraint 10 is removable, as illustrated in FIG. 6. The portion of the patient to be X-rayed can still be placed on the pad 34 of restraint 10 for the taking of the X-rays. The portion to be X-rayed can be secured to restraint 10 using the straps (not shown) or can merely be placed on the pad. An X-ray cassette 100 can be positioned on platform 12 between pad 34 and the remaining sidewall 15 as illustrated. To maintain cassette 100 in its vertical configuration, a magnet 102 is attached to sidewall 15 by string 104, and can be attached to the back of the X-ray cassette to hold it in position. The X-rays can thus be taken from the side using the medical restraint 10 of the present invention without interference from the sidewalls thereof.

In certain situations it is desirable that the portion of the patient to be X-rayed be held at an angle with respect to the X-ray table. As illustrated in FIG. 7, platform 12 of restraint 10 is connected to suction cups such as 49, 46 by armatures 50, 51. Armatures 50, 51 are pivotably connected to the suction cups at 110, 111 at the outside ends of the armatures. The inside ends of armatures 50, 51 terminate in inwardly directed rachet assemblies 112, 113. As illustrated in more detail by way of reference to FIG. 8, each inwardly directed rachet such as 112 has a serrated surface 115 on rachet 116. Rachet 116 is attached to the underside of platform 12, and corresponding rachets 112, 116 can be fixed together by engaging the threaded bolt 118 with wing nut 119. When the rachet members are compressed together using wing nut 119, the angular position of armature 50 is fixed. Hence, armatures 50, 51 and corresponding armatures on the opposite side of platform 12 can be used to mount the platform to the X-ray table at any desired angle.

The preferred configuration of the medical restraint 10 of the present invention is illustrated in more detail by way of reference to FIGS. 9 and 10 in combination. It is apparent therefrom that corresponding pairs of slots 120, 121 and 122, 123 are located on opposite sides of pad 34 between the pad and the respective sidewalls 14, 15. As illustrated in FIG. 10, straps such as 45 are adapted to pass upwardly through corresponding pairs of slots of opposite sides of pad 34 and meet above the pad. One end 124 of each strap has a section of eye material 125 and the other end 126 of the strap has a second of hook material 127. Such hook and eye materials are fabric fasteners ordinarily sold under the trade name Velcro, and are engageable to interconnect the respective ends of the strap and fix it around the portion of the patient to be restrained. Additional restraint can be placed on that portion of the patient by engaging the patient with sidewalls 14, 15, at least one of which is movable platform 12. Sidewalls 14, 15 are provided with pads 128, 129 on the insides thereof to minimize the discomfort of the patient when held in the restraint.

It is apparent that for the various purposes in which the restraint 10 of the present invention can be used, it may be desirable to vary the width of pad 34 and its supporting spacer 36. To this end, pad 34 and spacer 36 are fixed to platform 12 by snaps 38, 39 which can be detached from the spacer for the insertion of a different spacer and pad. Also, it may be desirable to remove the pad and spacer for cleaning and replace it on the platform. Spacers 36 of varying thickness and different configurations of the pad 34 may also be employed.

It is sometimes necessary, when obtaining the X-rays of a patient's torso or abdominal area, that the patient hold his or her arms in an outstretched position. Getting the patient to assume and hold this position becomes particularly difficult when the patient is a small child. Thus, the medical restraint of the present invention can be modified, as illustrated by FIG. 11, to include hollow restraint tubes 140, 142 which extend outward from apertures 144 and 145 formed in sidewalls 14 and 15, respectively. The tubular restraints 140, 142 are axially aligned with each other and may be attached to the sidewall apertures by a number of methods such as, for example, a threaded connection so that the tubes may be attached to or removed from the sidewalls of restraint 10.

In use, the child would insert his arms into and through the arm restraint tubes 140 and 142. The sidewalls can then be positioned snugly on each side of the child (FIG. 14). If required, straps 44, 45 can be applied to restrain the child in position for taking X-rays.

Turning now to FIGS. 12 and 13, the restraint support, referred to generally by numeral 150, may now be described. Support 150 includes a backplate 152 with a frontplate 154 mounted thereon in overlying relation. Frontplate 154 is held to backplate 152 by runner-like guides 156, 158 which are attached to the vertical side edges 160, 162 of the backplate. Guides 156, 158 are U-shaped in section and are dimensional so that frontplate 154 is held contiguous to backplate 152, yet is movable vertically.

The frontplate 154 is provided with a number of apertures 164 proximate the vertical side edges 166, 168 of the frontplate, which receive lock pins 170 and 172 through holes 174 placed in guides 156, 158. Thus, frontplate 154 can be moved, relative to backplate 152, by sliding the frontplate in the guides to the desired position. Pins 170, 172 are then inserted to hold the frontplate in fixed relation relative to the backplate. Movement of the frontplate by the user is facilitated by providing the frontplate with hand-hold 175.

The support 150 is mounted to an X-ray table 176 by suction cups 180. A pair of L-shaped support bars 182, 184 connect the suction cups to the backplate 152 to hold the backplate in an upright position relative to the X-ray table. The suction cups 180 sufficiently hold support 150, when in use, so that movement of the support in the longitudinal direction of the table is minimized.

To obviate any possible lateral movement of the support 150, relative to the X-ray table to which it is attached, braces 182, 184 are provided the support. Braces 182, 184 each include a shaft 186 and a clamp tab 188 depending perpendicular from one end of the shaft. The braces 182, 184 are mounted to backplate 152 by shaft housings 187, 188 respectively, which slidably hold the shaft 186 of each brace. The braces can be adjusted to grip the sides of an X-ray table and then caused to be fixedly held with their respective housings by tightening set screws 192, 194. Note that this particular method of mounting braces 182, 184 allows the restraint support 150 to be used on X-ray tables of different widths.

If desired, the table facing surface 196 of each clamp tab 188 can be provided with a rubber facing (not shown) to maximize the purchase obtained upon the X-ray table by the braces.

Preferably, backplate 152, frontplate 154 and even the frontplate guides 156, 158 are fabricated from a radiotranslucent material so that the support 150 will not cause shadows or other radiographic obstructions thereby avoiding superimposed images or other artifacts.

Connected to guide 156 of support assembly 150 is a spring-loaded retracting mechanism 198 which retracts and holds cord 200. The outer end of cord 200 has attachment ring 202 affixed thereto while disposable whistle 204 is removably attached to the cord itself. The cord 200 is of sufficient length so that it can be extended from the retracting mechanism 198 and ring 202 slipped over the ring pin 206, attached to guide 158, to hold the cord so extended. Whistle 202 can then be moved along the cord and placed in the mouth of a child being restrained by the complete assembly. The whistle not only aids in restraining the child by pacifying him to some extent, but also allows the X-ray technician to determine when the child inhales and exhales.

When the (X-ray) examination is finished, or the child is to be repositioned, the whistle may be removed from the child's mouth and the cord 202 allowed to retract by the retracting mechanismm 198 to move the whistle and cord out of the way. When the examination is complete, the whistle can be removed from the cord, disposed of, and replaced by another.

Use of restraint 10 and restraint support 150 as a restraint assembly can be seen by reference to FIGS. 14 and 15. In FIG. 14, restraint 10 is attached to frontplate 154 of restraint support 150 which, in turn, is mounted to X-ray table 200. The child 202 is seated on the X-ray table, his or her arms inserted in restraint tubes 140, 142 and is securely fastened to the restraint, as described, to immobilize the child for the radiographic process. Alternately, of course, restraint 10 need not be provided restraint tubes 140, 142 if the child's arms need not be outstretched.

Referring now to FIG. 15, there is illustrated the use of the restraint assembly for immobilizing the child's head. Note that restraint 10 need not be removed from frontplate 154 of support 150 and re-attached at the desired height. Rather, restraint 10 can be left mounted to frontplate 154. The technician merely removes pins 170, 172, slides the frontplate in a vertical direction by grasping hand-hold 175 and lifting, until the restraint is at the proper height. Pins 170, 172 are then inserted through holes 174 of the guides and into the frontplate to hold it in the position obtained.

While a preferred embodiment of the present invention has been illustrated in detail, it is apparent that modifications and adaptations of that embodiment will occur to those skilled in the art. For example, various mechanisms for holding the sidewalls in place along the width of the platform could be devised. However, it is to be expressly understood that such modifications and adaptations are within the spirit and scope of the present invention, as set forth in the following claims.

What I claim as new is:

1. A restraint assembly for positioning and holding a patient for radiography, said assembly comprising, in combination:
   a. support apparatus removably mounted to a horizontal, planar surface and extending generally upward therefrom, said support apparatus including:
      i. a backplate having opposed front and back planar surfaces;

ii. a frontplate positioned in parallel, confronting relation to the front surface of the backplate;

iii. guide means for slidably holding the frontplate in confronting, parallel relation to the front surface of the backplate and for allowing movement of the frontplate relative to the backplate;

iv. means attached to the backplate for removably affixing the support assembly to the horizontal surface; and b. restraint means removably attached to the frontplate of the support apparatus for restraining a portion of the patient in a fixed position for the taking of X-rays, the restraint means including a platform, means for releasably mounting the platform to the frontplate, a pair of sidewalls attached to the platform in spaced-apart opposed relation, at least one of said sidewalls being movable relative to the other sidewalls so that the portion of the patient can be restrained when secured between the sidewalls.

2. The restraint assembly of claim 1, wherein each of the sidewalls is provided with portions defining an aperture therein, the restraint assembly including an elongate hollow member affixed to each of the sidewalls in communicating relation with the aperture and extending outward from the sidewall pair.

3. The restraint assembly of claim 1, wherein the guide means allows the frontplate to be slidably movable in a plane parallel to the backplate and vertical to the horizontal surface.

4. The restraint assembly to claim 1, including whistle means affixed thereto for removable insertion into the mouth of a patient.

5. The support assembly of claim 1, wherein the mounting means includes a first plurality of suction cups attached to the backplate for mounting backplate to the horizontal surface.

6. The restraint assembly of claim 5, wherein the horizontal planar surface includes a pair of opposed side edges, the support apparatus is mounted generally transverse said edges, the mounting means includes clamp members for gripping said side edges to limit movement of the support assembly.

7. The restraint assembly of claim 1, wherein the restraint includes means for holding an X-ray cassette intermediate the restraint means and the support assembly to which it is attached.

8. The restraint assembly of claim 1, wherein the frontplate is fabricated from a radiolucent material.

9. The restraint assembly of claim 8, wherein the frontplate-fastening means is fabricated from a radiolucent material.

10. A restraint for holding a portion of a patient such as the head or a limb in a fixed position on an X-ray table for the taking of X-rays, said restraint comprising:

a platform having at least one laterally spaced pair of slot formed therein;

means for mounting the platform to the X-ray table including a plurality of elongate support elements, each of the support members having one end pivotally attached to the platform, the opposite end of each of the support elements having a suction cup pivotally attached thereto;

a padded surface overlying the platform intermediate the slots and attached to the platform, said padded surface adapted to receive and support the portion of the patient to be restrained thereupon;

a strap adapted to pass upwardly through the slots and around the portion of the patient to be restrained;

means for fastening the ends of the straps around the portion of the patient to be restrained; and a pair of sidewalls attached to the platform on opposite sides of the padded surface, at least one of said sidewalls being movable with respect to the padded surface so that the portion of the patient to be restrained can be secured between said sidewalls.

11. The restraint of claim 10, wherein said one sidewall is removable from the platform, and wherein the other sidewall includes means for restraining an X-ray cassette in an upraised position against said other sidewall for taking X-rays from the side.

12. The restraint of claim 10, wherein the padded surface has a raised step portion.

13. The restraint of claim 10, wherein the padded surface is removable from the platform for cleaning.

14. The restraint of claim 10, wherein one sidewall is removable from the platform to allow for the taking of X-rays from the side.

15. The restraint of claim 10, including a spacer intermediate the padded surface and the platform to elevate the padded surface.

16. The restraint of claim 10, wherein the mounting mean includes a pair of said elongate support elements attached to opposite sides of the platform and wherein the pivotal attachment between each of the support elements, the platform, and each of the respective suction cups includes fastening means for selectively positioning and holding the angular position of each of the pivotal attachments.

* * * * *